United States Patent
Arbore et al.

(10) Patent No.: US 10,274,426 B2
(45) Date of Patent: Apr. 30, 2019

(54) OPTICAL INSPECTION SYSTEM AND METHOD INCLUDING ACCOUNTING FOR VARIATIONS OF OPTICAL PATH LENGTH WITHIN A SAMPLE

(71) Applicant: Apple Inc., Cupertino, CA (US)

(72) Inventors: Mark Alan Arbore, Los Altos, CA (US); Matthew A. Terrel, Campbell, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 15/717,651

(22) Filed: Sep. 27, 2017

(65) Prior Publication Data

US 2018/0017491 A1    Jan. 18, 2018

Related U.S. Application Data

(63) Continuation of application No. 15/529,450, filed as application No. PCT/US2015/067463 on Dec. 22, 2015, now abandoned.
(Continued)

(51) Int. Cl.
*G01N 21/00* (2006.01)
*G01N 21/59* (2006.01)
(Continued)

(52) U.S. Cl.
CPC ............. *G01N 21/59* (2013.01); *G01N 21/49* (2013.01); *G01N 2021/1782* (2013.01);
(Continued)

(58) Field of Classification Search
None
See application file for complete search history.

(56) References Cited

U.S. PATENT DOCUMENTS

| 4,810,077 A | 3/1989 | Sting |
| 4,827,125 A | 5/1989 | Goldstein |

(Continued)

FOREIGN PATENT DOCUMENTS

| EP | 0 168 983 A1 | 1/1986 |
| EP | 0 943 950 A1 | 9/1999 |

(Continued)

OTHER PUBLICATIONS

Aguirre, A. D. et al. (Feb. 17, 2010). "High speed optical coherence microscopy with autofocus adjustment and a miniaturized endoscopic imaging probe," Optical Society of America, vol. 18, No. 5, Retrieved from the Internet: URL:http://www.ncbi.nlm.nih.gov/pmc/articles/PMC2906909/pdf/oe-18-5-4222.pdf , retrieved on Oct. 31, 2014, figures 1, 7, p. 4226-4235.
(Continued)

*Primary Examiner* — Shawn Decenzo
*Assistant Examiner* — Jarreas C Underwood
(74) *Attorney, Agent, or Firm* — Morrison & Foerster LLP (57) ABSTRACT

An illuminator/collector assembly can deliver incident light to a sample and collect return light returning from the sample. A sensor can measure ray intensities as a function of ray position and ray angle for the collected return light. A ray selector can select a first subset of rays from the collected return light at the sensor that meet a first selection criterion. In some examples, the ray selector can aggregate ray intensities into bins, each bin corresponding to rays in the collected return light that traverse within the sample an estimated optical path length within a respective range of optical path lengths. A characterizer can determine a physical property of the sample, such as absorptivity, based on the ray intensities, ray positions, and ray angles for the first
(Continued)

subset of rays. Accounting for variations in optical path length traversed within the sample can improve accuracy.

20 Claims, 7 Drawing Sheets

Related U.S. Application Data (60) Provisional application No. 62/096,276, filed on Dec. 23, 2014.

(51) Int. Cl.
    *G01N 21/49*     (2006.01)
    *G01N 21/17*     (2006.01)
    *G01N 21/47*     (2006.01)

(52) U.S. Cl.
    CPC ............ *G01N 2021/4709* (2013.01); *G01N 2021/4711* (2013.01); *G01N 2201/066* (2013.01); *G01N 2201/0691* (2013.01); *G01N 2201/0696* (2013.01); *G01N 2201/12* (2013.01)

(56) References Cited

U.S. PATENT DOCUMENTS

| | | | |
|---|---|---|---|
| 4,975,581 A * | 12/1990 | Robinson | A61B 5/14532 250/339.09 |
| 5,065,008 A | 11/1991 | Hakamata et al. | |
| 5,475,235 A * | 12/1995 | Phillips | H01S 5/042 250/574 |
| 5,483,261 A | 1/1996 | Yasutake | |
| 5,488,204 A | 1/1996 | Mead et al. | |
| 5,825,352 A | 10/1998 | Bisset et al. | |
| 5,835,079 A | 11/1998 | Shieh | |
| 5,880,411 A | 3/1999 | Gillespie et al. | |
| 5,936,739 A * | 8/1999 | Cameron | G01N 21/4795 356/441 |
| 5,946,100 A | 8/1999 | Ishihara | |
| 6,122,042 A | 9/2000 | Wunderman et al. | |
| 6,188,391 B1 | 2/2001 | Seely et al. | |
| 6,248,988 B1 | 6/2001 | Krantz | |
| 6,310,610 B1 | 10/2001 | Beaton et al. | |
| 6,323,846 B1 | 11/2001 | Westerman et al. | |
| 6,353,226 B1 | 3/2002 | Khalil et al. | |
| 6,424,416 B1 | 7/2002 | Gross et al. | |
| 6,519,033 B1 * | 2/2003 | Quist | G01N 15/14 356/337 |
| 6,587,703 B2 | 7/2003 | Cheng et al. | |
| 6,690,387 B2 | 2/2004 | Zimmerman et al. | |
| 6,794,658 B2 | 9/2004 | MacAulay et al. | |
| 7,015,894 B2 | 3/2006 | Morohoshi | |
| 7,184,064 B2 | 2/2007 | Zimmerman et al. | |
| 7,372,985 B2 | 5/2008 | So et al. | |
| 7,433,042 B1 * | 10/2008 | Cavanaugh | G01J 3/02 356/419 |
| 7,440,659 B2 | 10/2008 | Liu et al. | |
| 7,460,248 B2 | 12/2008 | Kurtz et al. | |
| 7,663,607 B2 | 2/2010 | Hotelling et al. | |
| 8,040,495 B2 | 10/2011 | Hendriks et al. | |
| 8,140,147 B2 | 3/2012 | Maynard et al. | |
| 8,479,122 B2 | 7/2013 | Hotelling et al. | |
| 8,547,535 B2 | 10/2013 | Tezuka et al. | |
| 8,619,237 B2 | 12/2013 | Hillman et al. | |
| 8,866,107 B2 | 10/2014 | Cui | |
| 8,958,858 B2 | 2/2015 | Tezuka et al. | |
| 9,013,684 B2 | 4/2015 | Xalter et al. | |
| 9,395,293 B1 | 7/2016 | Acosta et al. | |
| 9,442,084 B2 * | 9/2016 | Kakefuda | G01N 23/207 |
| 9,494,535 B2 * | 11/2016 | Sezginer | G01N 23/201 |
| 9,597,024 B2 * | 3/2017 | Robinson | A61B 5/14552 |
| 2004/0113059 A1 | 6/2004 | Kawano et al. | |
| 2004/0212866 A1 | 10/2004 | Endo et al. | |
| 2006/0197753 A1 | 9/2006 | Hotelling | |
| 2007/0057211 A1 | 3/2007 | Bahlman et al. | |
| 2009/0310132 A1 | 12/2009 | Bennett et al. | |
| 2011/0184260 A1 * | 7/2011 | Robinson | A61B 5/14532 600/316 |
| 2012/0070817 A1 | 3/2012 | Wang et al. | |
| 2012/0147377 A1 | 6/2012 | Schleipen et al. | |
| 2012/0281258 A1 | 11/2012 | Sheblee et al. | |
| 2014/0043620 A1 * | 2/2014 | Ishii | G01B 11/24 356/601 |
| 2014/0192355 A1 | 7/2014 | Froigneux et al. | |
| 2016/0091368 A1 | 3/2016 | Fish et al. | |
| 2018/0017772 A1 | 1/2018 | Arbore | |
| 2018/0039055 A1 | 2/2018 | Arbore | |

FOREIGN PATENT DOCUMENTS

| | | | |
|---|---|---|---|
| JP | 2000-163031 A | | 6/2000 |
| JP | 2002-342033 A | | 11/2002 |
| KR | 10-2009-0116731 A | | 11/2009 |
| WO | WO 2006/086566 | * | 8/2006 |
| WO | WO-2006/086566 A2 | | 8/2006 |
| WO | WO-2016/106350 A1 | | 6/2016 |
| WO | WO-2016/106368 A1 | | 6/2016 |
| WO | WO-2017/184420 A1 | | 10/2017 |

OTHER PUBLICATIONS

International Search Report dated Apr. 1, 2016, for PCT Application No. PCT/US2015/067445, filed Dec. 22, 2015, five pages.

International Search Report dated Apr. 5, 2016, for PCT Application No. PCT/US2015/067480, filed Dec. 22, 2015, four pages.

Ke, S. et al. (Feb. 10, 2009) "Three-dimensional coherent transfer function for a confocal microscope with two D-shaped pupils," Applied Optics, Optical Society of America, Washington, DC; US, vol. 48, No. 5, pp. 810-817.

Kurugol, S. et al. (2011). "Semi-automated Algorithm for Localization of Dermal/Epidermal Junction in Reflectance Confocal Microscopy Images of Human Skin," Proc. of SPIE, vol. 7904, ten pages.

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

Non-Final Office Action dated Apr. 6, 2018, for U.S. Appl. No. 15/529,451, filed May 24, 2017, 22 pages.

* cited by examiner

OPTICAL INSPECTION SYSTEM AND METHOD INCLUDING ACCOUNTING FOR VARIATIONS OF OPTICAL PATH LENGTH WITHIN A SAMPLE

CROSS-REFERENCE TO RELATED APPLICATIONS

This application is a continuation of U.S. application Ser. No. 15/529,450, filed May 24, 2017, which is a National Phase Patent Application under 35 U.S.C. § 371 of International Application No. PCT/US2015/067463, filed Dec. 22, 2015, which claims priority to U.S. Provisional Patent Application Ser. No. 62/096,276 filed Dec. 23, 2014, which are hereby incorporated by reference in their entirety.

TECHNICAL FIELD

The present disclosure relates to an optical inspection system for optically characterizing a sample, which can account for variations of optical path length within the sample.

BACKGROUND

Many optical inspection systems deliver light to a sample, collect light reflected or scattered from the sample, and use the collected light to analyze a portion of the sample. It can be desirable to improve these optical inspection systems.

SUMMARY OF THE DISCLOSURE

An illuminator/collector assembly can deliver incident light to a sample and collect return light returning from the sample. A sensor, such as a Shack-Hartmann sensor, can measure ray intensities as a function of ray position and ray angle for the collected return light. A ray selector can select a first subset of rays from the collected return light at the sensor that meet a first selection criterion. In some examples, the ray selector can aggregate rays into binned signals, each binned signal corresponding to rays in the collected return light that traverse within the sample an estimated optical path length within a respective range of optical path lengths. A characterizer can determine a physical property of the sample, such as absorptivity, based on the ray intensities, ray positions, and ray angles for the first subset of rays. Accounting for variations in optical path length traversed within the sample can improve accuracy.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

An optical inspection system can deliver light to a sample, collect light reflected or scattered from the sample, use the collected light to determine a physical property of the sample, such as absorptivity or refractive index. For highly absorbing or scattering samples, the high absorption or scattering can reduce an intensity of a light ray propagating through a portion of the sample. This reduction in intensity can depend strongly on the optical path length traversed within the sample.

For instance, in some configurations that deliver light to a sample and collect light reflected from the sample, the illuminating light is delivered as cone of light, converging toward a particular location at or below a surface of the sample. Similarly, the collected light is retrieved from a cone of light, diverging away from the particular location in the sample. For these cones of light, different portions of the cone can traverse different optical path lengths within the sample. For instance, a light ray at the center of the cone can traverse an optical path within the sample that is shorter than a light ray at the edge of the cone.

The optical inspection system can account for differences in the optical path length traversed within the sample, as a function of ray location and angle within the collected light. For some samples, an incident light ray is likely to be redirected by a single scattering event within the sample, such as a reflection or a redirection from a particular particle within the sample, or from an interface between two internal structures within the sample.

For these samples, the optical inspection system can use the geometry of single scattering events to determine regions on a detector at which the optical path length traversed within the sample can be determined relatively accurately. For these regions, a ray striking the region can have a known optical path length within the sample, or can have a relatively tight distribution of optical path lengths within the sample. For instance, the regions can describe locations on the detector at which rays returning from the sample arise from a single scattering event within the sample. For some examples, these detector regions can be weighted relatively strongly when determining the physical property of the sample. The detector regions can be selected as a function of sample type, to best use available dynamic ranges of detector pixels, and so forth.

Similarly, the detector can have regions at which the optical path length traversed within the sample cannot be determined accurately. For these regions, a ray striking the region can have one of many optical path lengths within the sample, or can have a relatively broad distribution of optical path lengths within the sample. For instance, the regions can describe locations on the detector at which rays returning from the sample arise from multiple sequential scattering events within the sample. For these multiply scattered rays, there may be many possible paths within the sample. For some examples, these detector regions can be weighted relatively weakly or excluded when determining the physical property of the sample.

Figure 1:
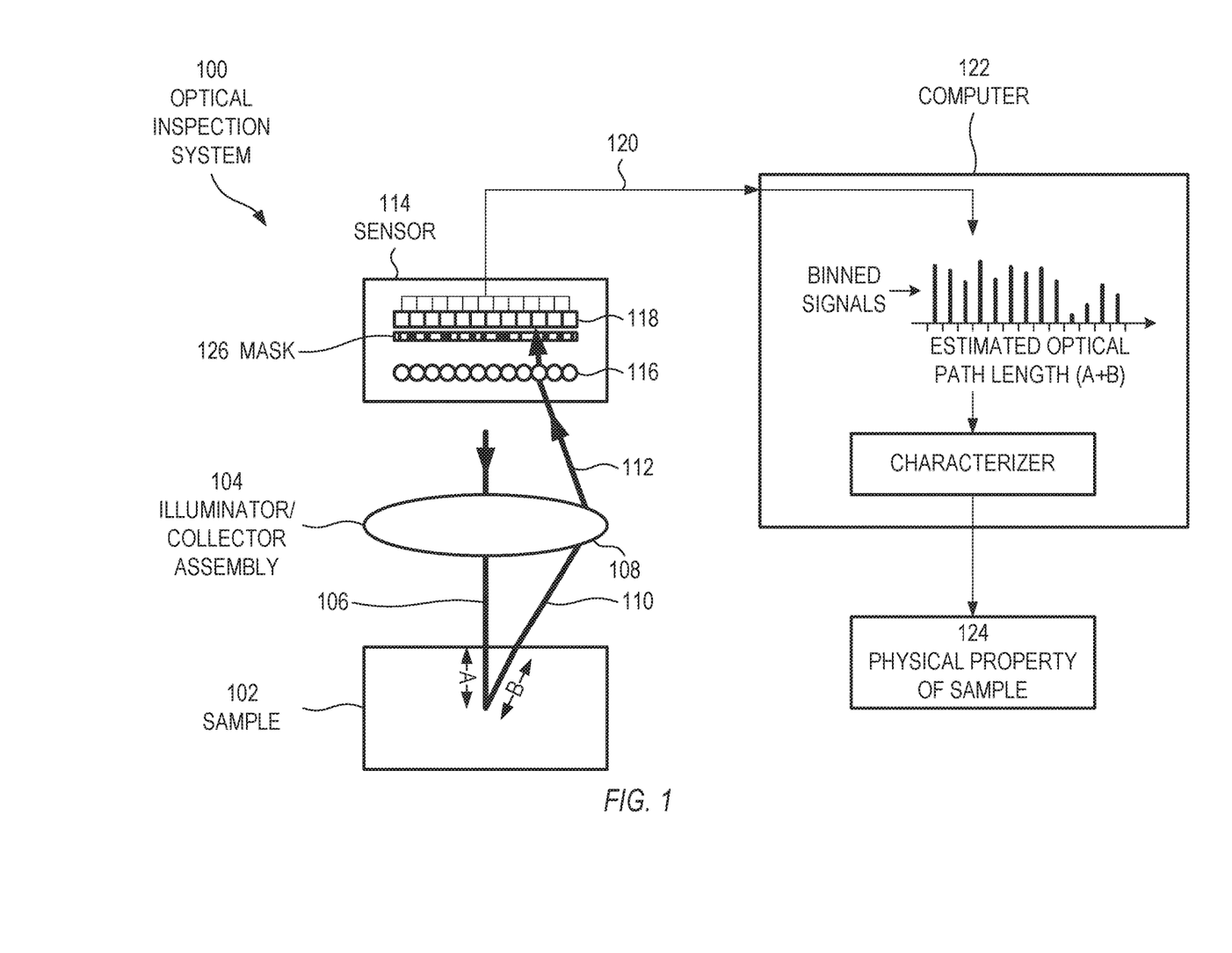
FIG. 1 shows an example of an optical inspection system for optically characterizing a sample, in accordance with some embodiments.

FIG. 1 shows an example of an optical inspection system 100 for optically characterizing a sample 102, in accordance with some embodiments. The sample 102 is not part of the optical inspection system 100. The optical inspection system 100 of FIG. 1 is but one example; other suitable optical inspection systems can also be used.

The optical inspection system 100 includes an illuminator/collector assembly 104. In some examples, the illuminator/collector assembly 104 is a single objective lens. In other examples, the illuminator/collector assembly 104 includes separate illumination optics and collection optics.

The illuminator/collector assembly 104 delivers incident light 106 to the sample 102. The incident light 106 can have a range of propagation angles at the sample 102. In some examples, the range can have an angular width less than or equal to 20 degrees. In other examples, the range can have an angular width less than or equal to 10 degrees. In some of these examples, the incident light 106 can be collimated, with a range having an angular width of effectively zero. In examples exhibiting refraction at the sampling interface, due to differing indices of refraction, the angular width at the sampling interface can be defined in the medium having the larger range of angles. In some examples, the incident light 106 includes more than one wavelength simultaneously, such as a plurality of discrete wavelengths or a relatively broad spectrum. In some examples, the incident light 106 includes one wavelength at a time, but the wavelength can be selectively shifted over time. In still other examples, the incident light 106 includes a relatively broad spectrum that shifts sequentially over time. In still other examples, the incident light 106 includes a plurality of relatively broad, non-overlapping spectral regions that all shift, together, over time. In some examples, the incident light 106 can be pulsed or modulated at one or more specified frequencies. In some examples, the incident light 106 can include multiple spectral regions, with each spectral regions being pulsed or modulated at its own unique frequency. In some examples, the illuminator/collector assembly 104 can include one or more light sources, such as a single semiconductor laser, multiple semiconductor lasers having the same wavelength, multiple semiconductor lasers having different wavelengths, a single light emitting diode, multiple light emitting diodes having the same wavelength, multiple light emitting diodes having different wavelengths, one or more quantum cascade lasers, one or more superluminescent light sources, one or more amplified spontaneous emission sources, any combination of the above, or other suitable light sources. In some examples, the illuminator/collector assembly 104 can further include one or more collimating and/or focusing optics, such as lenses, which can collimate and/or focus light produced by the one or more light sources. In some examples, the illuminator/collector assembly 104 can further include one or more beam-steering elements, such as a beamsplitter, which can reflect an incident beam and transmit a collected beam, or can transmit an incident beam and reflect a collected beam.

The illuminator/collector assembly 104 can deliver the incident light 106 to the sample 102 through a sampling interface 108. In the specific example of FIG. 1, the sampling interface 108 is a surface of an objective lens, the surface facing the sample 102. In some examples, the sampling interface 108 can be an outward-facing surface of a device, which is placed into contact with the sample 102 during operation. In some examples, the sampling interface 108 can be a cover glass, which is placed into contact with the sample 102 during operation. In some examples, the sampling interface 108 can be a lens surface or an optical surface that is spaced apart in air or another incident medium from the sample 102. In some examples, the sampling interface 108 can include separate first and second surfaces, where incident light passes through the first surface, and return light passes through the second surface.

The illuminator/collector assembly 104 can collect return light 110 returning from the sample 102 through the sampling interface 108 to form collected return light 112. In some examples, the incident light 106 and return light 110 pass through the same sampling interface 108.

A sensor 114 can receive the collected return light 112. Unlike a conventional multi-pixel detector, which is largely insensitive to ray angle, the sensor 114 can measure ray intensities as a function of ray position and ray angle for the collected return light 112. In the example of FIG. 1, the sensor 114 is a Shack-Hartmann sensor, which includes a microlens array 116 and a multi-pixel detector 118 at or near a focal plane of the microlens array 116. Another example of a suitable sensor 114 is an array of pinholes, with a multi-pixel detector disposed in an optical path after the array of pinholes. These are but two examples; other suitable sensors can also be used.

The sensor 114 can produce a plurality of signals 120 corresponding to the measured ray intensities. In some examples, the signals 120 are electrical. In other examples, the signals 120 are optical, such as with optical intensities in an optical fiber. In some examples, each pixel from the multi-pixel detector 118 can produce its own signal 120. In other examples, one or more groups of pixels can be optically or electrically coupled together to form the signals 120.

A computer 122 can receive the plurality of signals 120 from the sensor 114. In some examples, the computer 122 can aggregate at least some of the received signals into a plurality of binned signals. Each binned signal can be formed from corresponding rays striking the sensor 114. Each of the corresponding rays traverses a respective optical path length within the sample 102. In the example of FIG. 1, the optical path length traversed within the sample 102 by a ray of the incident light 106 is represented by the quantity A, and the optical path length traversed within the sample by a ray of the return light 110 is represented by the quantity B, so that the total optical path length traversed within the sample is represented by the quantity A+B. In some examples, it can be advantageous if the quantity A+B equals, or is on the order of, an inverse of an expected absorption coefficient of the sample 102; the Appendix discusses this in detail. For the binned signals, each binned signal can correspond to rays in the collected return light 112 that traverse within the sample 102 an estimated optical path length within a respective range of optical path lengths. In some examples, the ranges of optical path length can be adjoining.

The computer 122 can include a characterizer configured to determine a physical property 124 of the sample 102 based on the ray intensities, ray positions, and ray angles for a first subset of rays. The signals 120 can supply the ray intensities, ray positions, and ray angles to the computer 122. In some examples, the characterizer can perform a first operation set using the first subset of rays and perform a second operation set using a second subset of rays in determining a physical property 124 of the sample 102. The subsets are determined by a ray selector (discussed below).

In some examples, the characterizer can fit the one or more of the signals to a Beer's Law calculation. In some of these examples, the characterizer can determine an absorptivity of the sample 102 based on the Beer's Law calculation. In some of these examples, the characterizer can apply different weights to the signals when determining the absorptivity of the sample 102. Beer's Law describes how much light transmits through an absorptive or scattering sample. One example of a configuration for Beer's Law is $T(\lambda)=\exp(-L \times c \times a(\lambda))$, where $\lambda$ is the wavelength of light, L is the optical path length traversed within the sample by the light, $a(\lambda)$ is a wavelength-dependent absorptivity of substance within the sample, c is a concentration of the substance within the sample, and $T(\lambda)$ is a fraction of light exiting the sample. Other suitable configurations of Beer's Law can also be used. In some examples, the absorptivity is the output quantity from the optical inspection system 100. In other examples, the output quantity can be functionally equivalent to absorptivity, such as transmissivity or complex refractive index. In other examples, the absorptivity can be an intermediate quantity, which is used internally by the optical inspection system 100 to calculate one or more other physical properties of the sample 102, such as sample concentration, or other suitable physical properties.

The optical inspection system can include a ray selector. The ray selector can select the first subset of rays from the collected return light 112 at the sensor 114 that meet a first selection criterion. In some examples, the first selection criterion can include a first range of estimated path lengths, such as path lengths traversed within the sample 102 or path length distributions, such as distributions of path length traversed within the sample 102. In other examples, the first selection criterion can include a first range of estimated ray penetration depths within the sample 102. In some examples, the ray selector 116 can additionally select a second subset of rays from the collected return light 112 that meet a second selection criterion. For these examples, the first and second selection criteria can include first and second ranges of estimated path lengths or path length distributions. In other examples, the ray selector 116 can select more than two subsets of rays, with each subset having a corresponding selection criterion. Such subsets of rays can be referred to as bins, or binned rays.

In some examples, the ray selector can operate entirely in software. For instance, computer 122 can include a lookup table that maps each pixel at the multi-pixel detector 118 to a corresponding optical path traversed within the sample. The corresponding optical path within the sample can include ray position and ray angle at the sample 102 or at a suitable longitudinal location at or near the sample 102. Such a lookup table can be prepared by tracing rays through the geometry of the illuminator/collector 104 assembly and through any additional elements between the sample 102 and the sensor 114. Such a ray trace can be performed once, with the results being stored in the lookup table and accessible by the computer 122. From the lookup table, the computer 122 can group the detector pixels into bins, with each bin corresponding to a specified range of optical path lengths traversed within the sample 102. In some examples, the ray selector can receive signals from corresponding pixels of the detector 118, average a first subset of the signals to form a first binned signal, average a second subset of the signals to form the second binned signal, and average additional subsets of the signals to form additional binned signals. In some examples, the computer 122 is configured to aggregate signals from the multi-pixel detector 118 into binned signals, each binned signal corresponding to rays in the collected return light that traverse within the sample an estimated optical path length within a respective range of optical path lengths. In some of these examples, the ranges of optical path length can adjoin one another.

In other examples, the ray selector can operate at least in part in hardware. For these examples, at least some of the binning can occur at the hardware level. For instance, instead of using a grid of pixels at the detector, the detector area can instead be partitioned into shapes that correspond to the bins discussed above. In this example, each detector area can receive rays that traverse an optical path length within the sample, within a specified range of optical path lengths. In some of these examples, each detector area can produce a respective signal 120, which is directed to the computer 122. In some examples, the ray selector can include first and second pixels of the sensor, where the first and second pixels are shaped and sized to measure ray intensities for rays within the first and second subsets of rays. For these examples, the first and second pixels can respectively output the first and second binned signals. As another example, the detector can use a grid of pixels, and each pixel can produce its own signal, but the signals are combined in hardware prior to delivery at the computer 122.

In still other examples, the ray selector can operate in a combination of software and hardware, with some of the binning occurring at the sensor 114 and/or at the signal level, and some of the binning occurring at the computer 122.

For each location at the detector 118, it can be possible to calculate a corresponding estimated optical path traversed within the sample. However, the reliability of the calculations can vary from location-to-location at the detector. For some geometries, such as the geometry associated with a single scattering event (discussed below in detail), the calculation can be relatively reliable.

In some examples, the optical inspection system 100 can set a specified threshold for reliability. Signals from detector locations exceeding the threshold can be used for subsequent calculations, and signals from detector locations below the threshold can be excluded from use in the subsequent calculations. For some of these examples, the optical inspection system 100 can include an optional mask 126 positioned between the microlens array 116 and the multi-pixel detector 118. The mask 126 can block rays for which the optical inspection system 100 cannot reliably determine the optical path length traversed within the sample. In some examples, the mask 126 can be directly adjacent to, in contact with, or deposited on the multi-pixel detector 118. The mask 126 can include at least one blocking portion, which blocks specified rays in the collected return light 112. The mask 126 can block particular pixels on the multi-pixel detector 118. In some examples, the mask 126 is stationary over time. For instance, the mask 126 can be formed as a coating on an optical surface, where the coating includes reflective, transmissive, and/or absorptive portions that do not change over time. In other examples, the mask 126 can be reconfigurable over time. For instance, the mask 126 can be formed as a reconfigurable panel, such as an array of micromirrors, which can selectively direct portions of the collected return light 112 toward the detector 118 or away from the detector 118, and can change which portions are directed toward the detector 118 or away from the detector 118 as needed. Alternatively, the thresholding can be performed in combination with the computer 122 or entirely in software by the computer 122.

In some examples, rather than use a single threshold value, the optical inspection system 100 can assign relative weights to the binned signals. Each weight can represent a confidence level that the optical path lengths within the sample 102 are the same, or are within a specified range for all of the rays in the corresponding bin. In some examples, the relative weight varies inversely with a width of an estimated distribution of the respective optical path lengths for the binned signal. In these examples, the term inverse is intended to signify a monotonic relationship between relative weight and distribution width, without requiring a mathematically proportional relationship. For instance, as the width of an estimated distribution decreases, the relative weight can increase. As another example, as the width of an estimated distribution increases, the relative weight can decrease. In some examples, each of the corresponding rays, when traced back through the illuminator/collector assembly 104, passes a respective distance away from a corresponding incident ray within the incident light, and the relative weight varies inversely with the respective distance. In some examples, the weight of each binned signal corresponds to a probability that light that generated the binned signal originated from a single scattering event in the sample. FIGS. 2-7 and the accompanying discussion below address the geometry of a single scattering event.

The computer 122 can be included in a computer system that includes hardware, firmware and software. Binning electrical signals, assigning relative weight to the binned electrical signals, determining a physical property, as well as some intermediate computational tasks, such as tracing rays and characterizing, can be executed in software, or executed in digital electronic hardware in which the ray tracing and characterizing are hard-wired into the hardware; for the purposes of this document, such hard-wired digital electronic hardware is considered to be executing ray tracing software and/or a characterizer. Examples may also be implemented as instructions stored on a computer-readable storage device, which may be read and executed by at least one processor to perform the operations described herein. A computer-readable storage device may include any non-transitory mechanism for storing information in a form readable by a machine (e.g., a computer). For example, a computer-readable storage device may include read-only memory (ROM), random-access memory (RAM), magnetic disk storage media, optical storage media, flash-memory devices, and other storage devices and media. In some examples, computer systems can include one or more processors, optionally connected to a network, and may be configured with instructions stored on a computer-readable storage device.

FIGS. 2-7 address a particular geometry associated with a single scattering event in the sample. For rays satisfying this geometry, the optical path traversed within the sample can be determined with a relatively high degree of confidence. It is instructive to explore the single scattering event geometry in detail.

Figure 2:
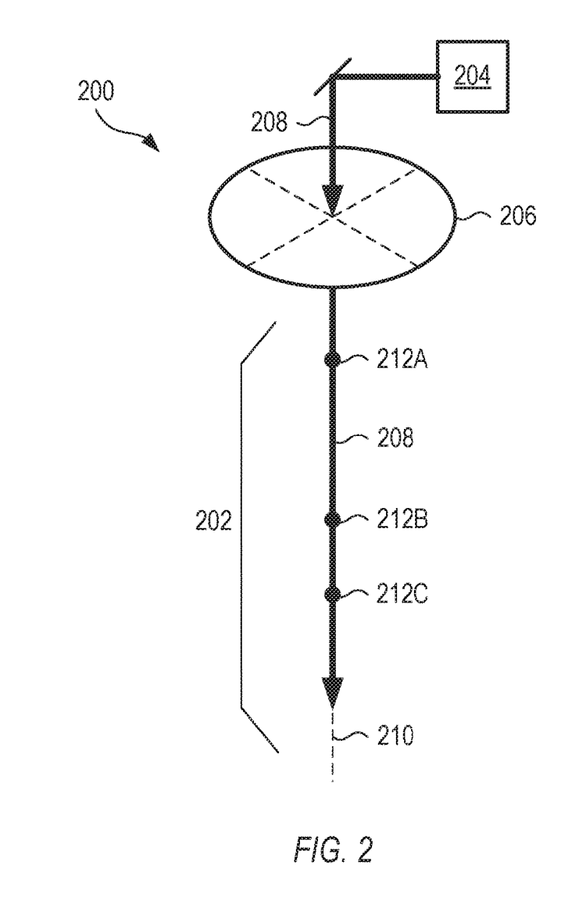
FIG. 2 shows a portion of an incident optical path in an example of an optical inspection system, in accordance with some embodiments.

FIG. 2 shows a portion of an incident optical path in an example of an optical inspection system 200, in accordance with some embodiments. Incident light 208 from a light source 204, optionally redirected by a mirror, strikes a central portion of a pupil of an illuminator/collector assembly 206, and propagates within sample 202 generally coincident with a central axis 210 of the illuminator/collector assembly 206. The incident light 208 is shown in FIG. 2 as passing through three scattering events 212A, 212B, 212C. In practice, each of the scattering events 212A, 212B, 212C can redirect a fraction of the incident light 208 into a respective redirected ray, with the remaining fraction continuing to propagate away from the illuminator/collector assembly 206 along the central axis 210. It will be understood that the configuration of FIG. 2, and the use of three discrete scattering events, is but one example, and that other configurations can also be used. It will also be understood that the incident optical path does not necessarily have to be coincident with the optical axis.

Figure 3:
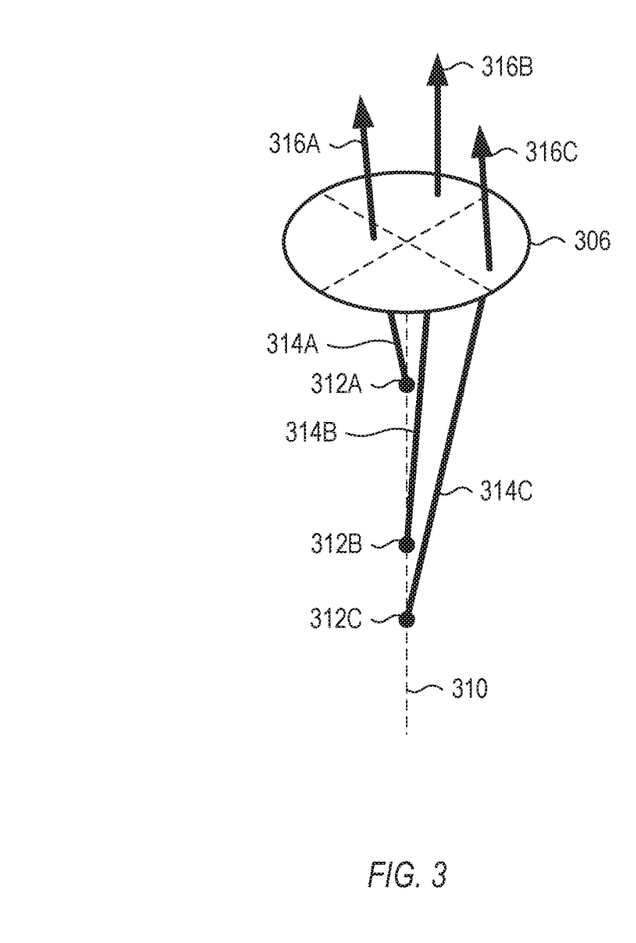
FIG. 3 shows a portion of a return optical path in an example of an optical inspection system, in accordance with some embodiments.

FIG. 3 shows a portion of a return optical path in an example of an optical inspection system, in accordance with some embodiments. Elements numbered 300-312 in FIG. 3 are identical in structure and function to similarly numbered elements 200-212 in FIG. 2. Light rays 314A, 314B, 314C arise from respective scattering events 312A, 312B, 312C. The illuminator/collector 306 collects and redirects rays 314A, 314B, 314C to form return rays 316A, 316B, 316C.

Figure 4A:
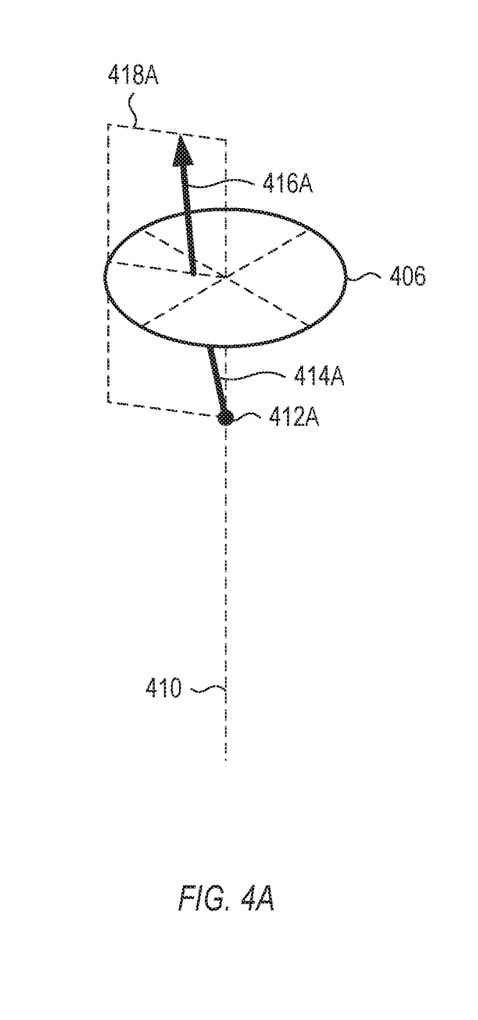
FIGS. 4A, 4B, and 4C are individual views of the three light rays in the return optical path of FIG. 3, in accordance with some embodiments.
Figure 4B:
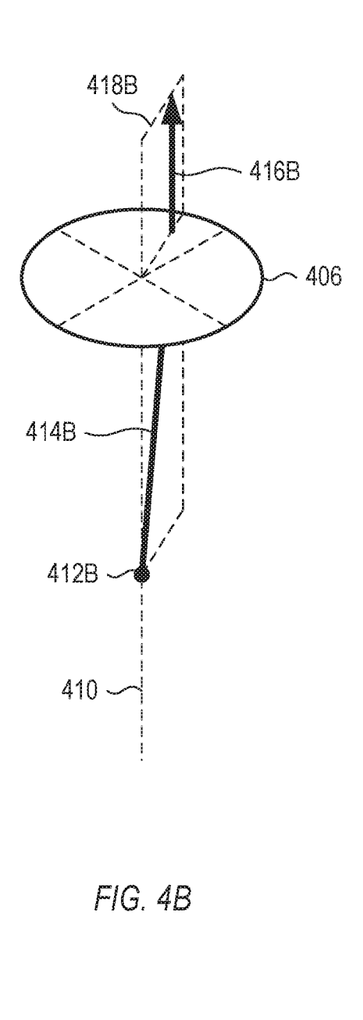
Figure 4C:
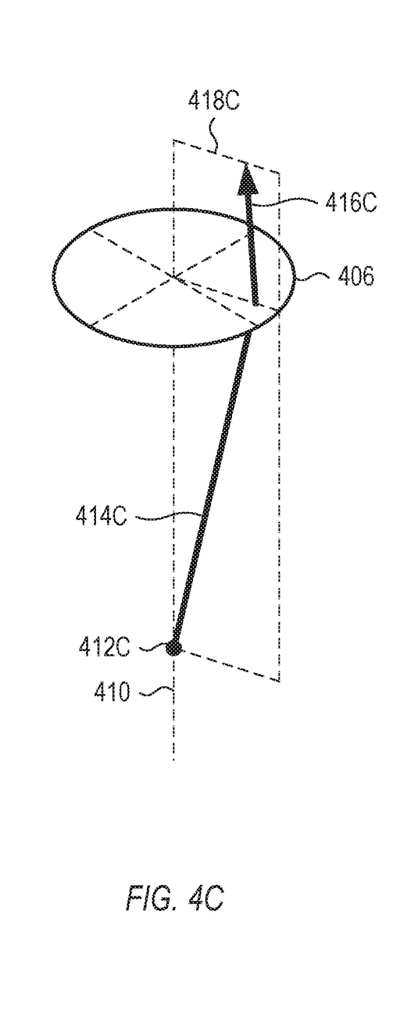

FIGS. 4A, 4B, and 4C are individual views of the three light rays in the return optical path of FIG. 3, in accordance with some embodiments. Because rays 416A, 416B, 416C originate from points along the central axis 410 of the illuminator/collector assembly 406, rays 416A, 416B, 416C propagate within respective planes 418A, 418B, 418C, all of which include the central axis 410 of the illuminator/collector 406.

Figure 5:
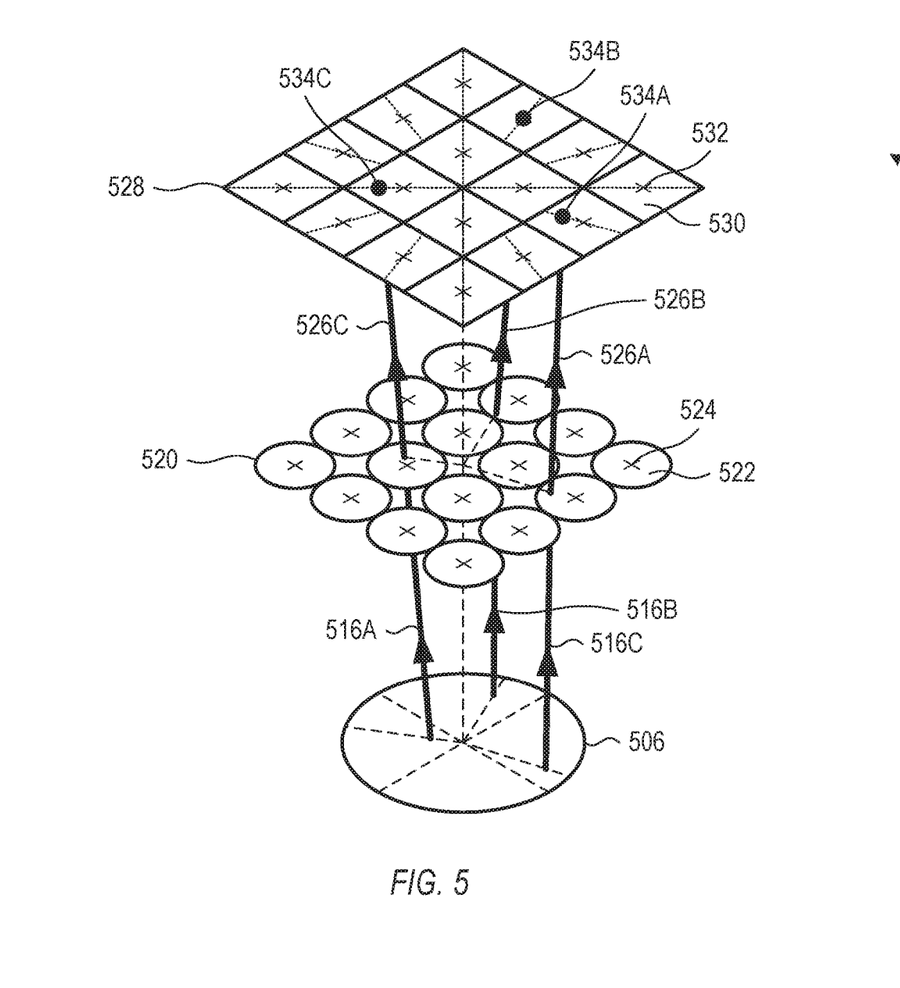
FIG. 5 shows the rays of FIGS. 4A, 4B, and 4C, traced from the illuminator/collector assembly, to the array of microlenses, to the detector, in accordance with some embodiments.

FIG. 5 shows the rays of FIGS. 4A, 4B, and 4C, traced from the illuminator/collector assembly 506, to the array 520 of microlenses 522, to the detector 528, in accordance with some embodiments. The detector 528 can include a plurality of zones 530 in a one-to-one correspondence with the array 520 of microlenses 522. Each zone 530 can have a center 532 corresponding to a center 524 of a respective microlens 522. The array 520 of microlenses 522 redirects rays 516A, 516B, 516C to form rays 526A, 526B, 526C, which strike detector 528 at locations 534A, 534B, 534C.

Figure 6:
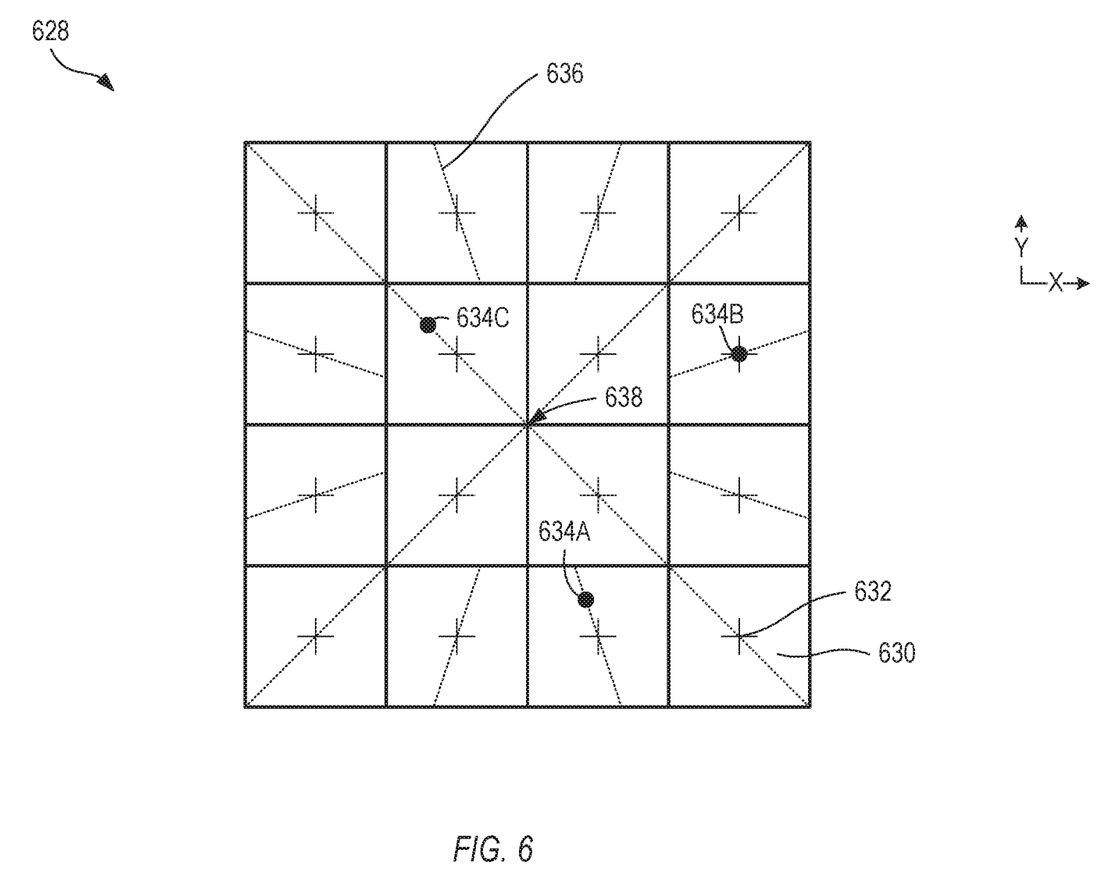
FIG. 6 shows an end-on view of the detector from FIG. 5, in accordance with some embodiments.

FIG. 6 shows an end-on view of the detector 628 from FIG. 5, in accordance with some embodiments. Each zone 630 can include a respective region 636 at which rays propagating from the sample to the Shack-Hartmann sensor propagate in a plane that includes the central axis of the illuminator/collector assembly. The regions 636 can be linear, can be radially oriented with respect to the central axis of the illuminator/collector assembly or a center 638 of the detector 628, and can include a center 632 of the respective zone 630. Rays 526A, 526B, 526C (FIG. 5) strike the detector 628 at respective locations 634A, 634B, 634C. When the Shack-Hartmann sensor is positioned so that the array of microlenses is located at the Fourier plane, or the front focal plane, of the illuminator/collector, a distance away from the zone center 632 can be proportional to (or nearly proportional to, or related with a 1:1 correspondence to) a propagation angle of rays 516A, 516B, 516C (FIG. 5). Other possible arrangements include an input light that propagates in a direction, which is not coincident with a central axis of the optical inspection system.

In an alternate configuration, where the incident light has a slightly larger footprint and extends over an area that can include the central axis, the rays can be traced back through the illuminator/collector assembly, and can intersect corresponding incident rays within the incident light. For some of these configurations, the incident light can have a range of propagation angles at the sampling interface, where the range can have an angular width less than or equal to 20 degrees, or preferably less than or equal to 10 degrees. As the angular range increases, it becomes more difficult to accurately determine the optical path length traversed within the sample.

For rays that reside in (or sufficiently near) a plane that includes the central axis of the illuminator/collector assembly, the ray paths can be used to calculate respective optical path lengths traversed within the sample. The ray intensities can be correlated with the optical path lengths. The correlation can be used to determine a physical property of the sample, such as absorptivity, transmissivity, refractive index, and others. For other rays, which do not reside in (or sufficiently near) said planes, the optical path lengths cannot easily be calculated.

The propagation angle and location of a particular ray in the collected return light, such as 310 (FIG. 3) or 410 (FIG. 4), can determine whether or not the particular ray resides in a plane that includes the central axis (or, alternatively, the direction of the incident optical path). If the propagation angle and location of the ray show that the ray resides in one of said planes, then the contribution from the ray can be weighted relatively heavily to be used downstream to calculate the physical property of the sample. If the propagation angle and location of the ray show that the ray does not reside in one of said planes, then the contribution from the particular ray can be weighted relatively lightly to be used downstream to calculate the physical property of the sample.

One way to determine whether a particular ray resides in a plane that includes the central axis is to trace the ray backwards, through the illuminator/collector assembly, to the sample. There will be a particular longitudinal location at which the traced ray is a minimum distance from the central axis. This minimum distance for each traced ray can be used to determine a weight, such as relative weight, which indicates how confidently one can determine the optical path length traversed in the sample by the traced ray. If the traced ray intersects the central axis, the minimum distance is zero, and the weighting factor can be its maximum value. If the traced ray comes relatively close to the central axis, the weighting factor can be relatively high. If the traced ray passes relatively far from the central axis, the weighting factor can be relatively low. In some examples, the weighting factor for a traced ray can vary inversely with a minimum distance between the traced ray and the central axis.

In some examples, it can be beneficial to identify one or more detector regions, where it can be difficult to reliably determine an estimated optical path length traversed within the sample for a ray striking an identified region. For instance, the identified region or regions can correspond to one or more detector regions at which a confidence level of an estimated optical path length falls below a threshold value. Other suitable ways to determine the identified detector regions can also be used.

In some examples, rays in the one or more identified detector regions can be weighted more lightly than rays outside the identified detector regions, when determining the physical property of the sample. For instance, each detector pixel, or suitable group of detector pixels, can be assigned a relative weight. In some examples, the relative weight can represent a confidence level that the optical path lengths within the sample are the same. In some examples, the relative weight can represent a confidence level that the optical path lengths are similar, or are nearly the same, or span a range with a width that is within a specified percentage of the mean optical path length traversed within the sample for all the rays included in the respective bin. In other examples, the relative weight can vary inversely with a width of an estimated distribution of the respective optical path lengths within the sample. In still other examples, each ray in the collected light, when traced back through an illuminator/collector assembly, passes a respective distance away from a corresponding incident ray within the incident light, and the relative weight can vary inversely with the respective distance. In still other examples, the relative weight can correspond to a probability that corresponding rays originated from a single scattering event in the sample. Other weighting schemes are also possible.

In some examples, rays in the one or more identified detector regions can be excluded entirely when determining the physical property of the sample. One can consider this exclusion to be an extreme weighting, where excluded rays are assigned a weight of zero. In some examples, the exclusion can be performed in software, such as by a computer, such as 122 (FIG. 1). In other examples, the exclusion can be performed entirely in hardware, such as with a mask, such as 126 (FIG. 1).

Figure 7:
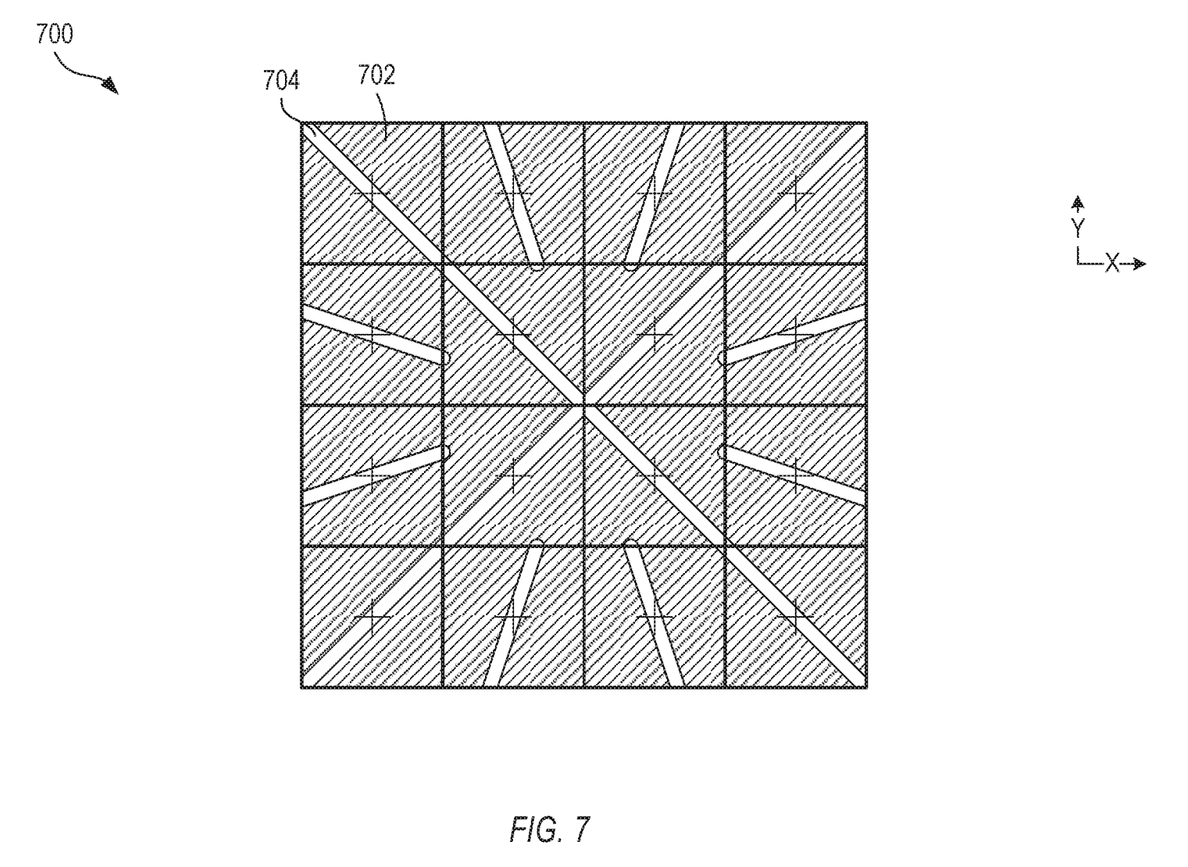
FIG. 7 shows an end-on view of an example of a mask disposed proximate the detector of FIG. 6, in accordance with some embodiments.

FIG. 7 shows an end-on view of an example of a mask 700 disposed proximate the detector of FIG. 6 in the Shack-Hartmann sensor, in accordance with some embodiments. Mask 700 blocks portions 1002 and transmits portions 1004 to the detector. In the example of FIG. 7, the mask 700 pass only rays that, when traced backward through the illuminator/collector assembly, pass within a threshold distance of the central axis of the illuminator/collector assembly. For this example, there are two bins. One bin, corresponding to rays that fall within transmitted portion 704, is used to calculate the physical property of the sample. This bin can have a relative weight of 100%, or another suitable measure. The other bin, corresponding to rays that fall within blocked portion 702, is not used to calculate the physical property of the sample. This bin can have a relative weight of 0%, or another suitable measure.

In the example of FIG. 7, the detector can be a multi-pixel detector, with pixels arranged in a rectangular pattern, and each pixel producing a corresponding electrical signal. Alternatively, the detector can be a multi-element detector, with regions having any suitable sizes and shapes, and each region producing a corresponding electrical signal. As a further alternative, the detector can be a single-element detector, producing a single electrical signal.

Figure 8:
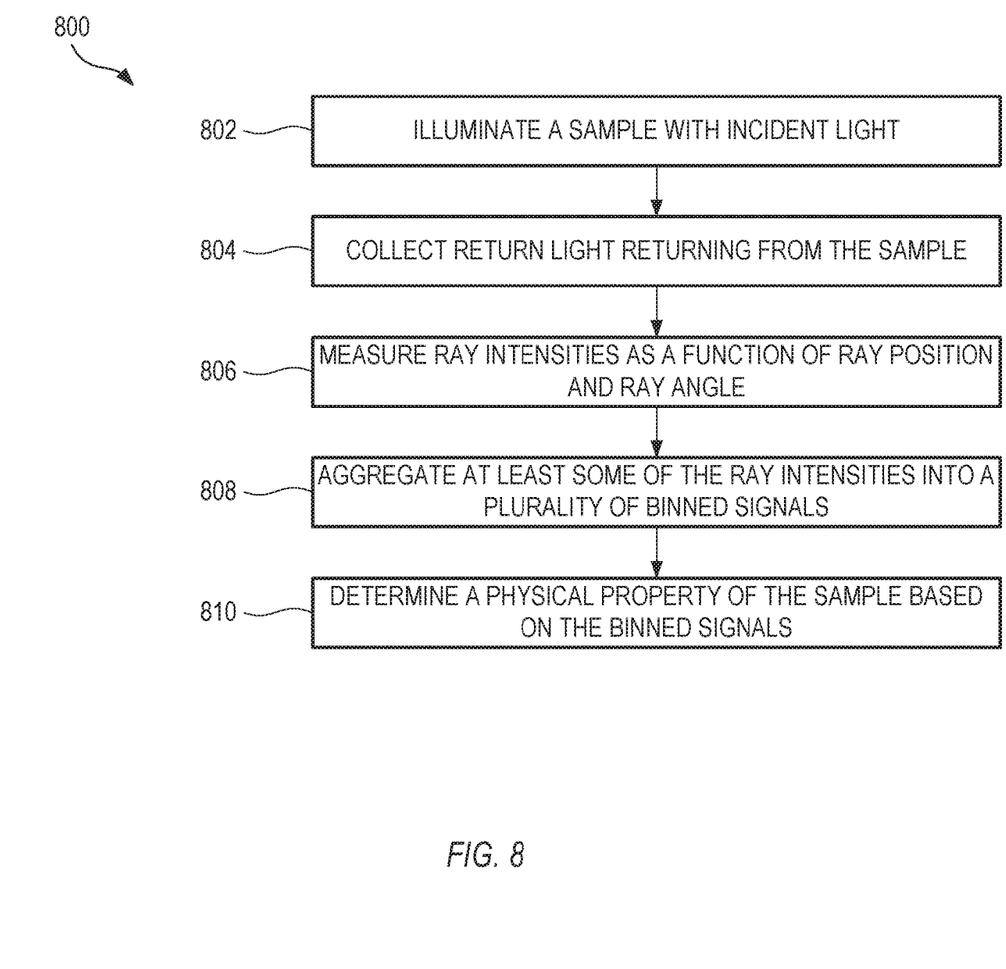
FIG. 8 shows a flow chart of an example of a method for optically characterizing a sample, in accordance with some embodiments.

FIG. 8 shows a flow chart of an example of a method 800 for optically characterizing a sample, in accordance with some embodiments. The method 800 can be executed on an optical inspection system, such as 100 (FIG. 1). Method 800 is but one example; other suitable methods for optically inspecting a sample can also be used.

At 802, method 800 illuminates the sample with incident light. At 804, method 800 collects return light returning from the sample to form collected return light. At 806, method 800 measures ray intensities as a function of ray position and ray angle for the collected return light. At 808, method 800 aggregates at least some of the electrical signals into a plurality of binned signals. The aggregation into bins can be performed purely in software, purely in hardware, or in a combination of software and hardware. At 810, method 800 determining a physical property of the sample based on the binned signals. In some examples, each binned signal can correspond to rays in the collected return light that traverse within the sample an estimated optical path length within a respective range of optical path lengths. In some examples, method 800 can further include fitting the binned signals to a Beer's Law calculation; and determining an absorptivity of the sample based on the Beer's Law calculation.

APPENDIX

The optical properties of a particular type of sample, such as human tissue, can vary from sample-to-sample, but often fall into a well-defined range of numerical values. For instance, a scattering coefficient of a particular sample typically falls within a particular range of scattering coefficients, where the range can represent a distribution of values of the scattering coefficient for a population of samples of the same type as the particular sample. The range can be centered around a so-called expected value, such as an expected scattering coefficient. In some examples, the expected values can be used when designing a geometry for an optical inspection system, with the expectation that most actual measured values will be relatively close to, but different from, the expected value.

In an optical inspection system designed to inspect a particular type of non-transparent sample, so that light propagating through the sample scatters and/or is absorbed by the sample as it propagates, the amount of scattering and/or absorption of the sample can influence the amount of light that reaches a detector in the optical inspection system. In other words, sample-to-sample variation of a scattering and/or absorption coefficient can produce a sample-to-sample variation in the optical power reaching a detector. Such sample-to-sample variation can be undesirable, and can underutilize a full dynamic range of the detector. It is possible to design the optical inspection system to have a decreased sensitivity of detected optical power to sample-to-sample variation in scattering coefficient.

An analytical model of the optical inspection system can assume that a light ray enters the sample at an input point, scatters a single time at a scattering location, changes direction just once at the scattering location, and exits the sample at an output point. In propagating from the input point to the scattering location, an input beam is attenuated by a factor $\exp[-A(\mu_s+\mu_a)]$, where quantities $\mu_s$ and $\mu_a$ are the scattering and absorption coefficients of the sample, respectively, and quantity A is an optical path length between the input point and the scattering location. At the scattering location, a fraction $\gamma\mu_s$ of the remaining input beam is scattered towards the output, where factor $\gamma$ accounts for a scattering phase function. The light scattered toward the output location is further attenuated by an amount $\exp[-B(\mu_s+\mu_a)]$ before exiting the sample, where quantity B is an optical path length between the scattering location and the output point. A fraction of optical power exiting the sample at the output location, divided by optical power entering the sample at the input location, is given by the quantity $\gamma\lambda_s \exp[-L(\mu_s+\mu_a)]$, where quantity L equals quantity A+B, and is a total optical path length traversed within the sample.

The fraction of optical power exiting the sample is relatively insensitive when its derivative equals zero, e.g., when the total optical path length traversed within the sample, L, equals an inverse of the scattering coefficient of the sample, $1/\mu_s$. When $L=1/\mu_s$, the optical power reaching the detector is maximized, which is beneficial, and is relatively insensitive to sample-to-sample variations in the amount of scattering, which is also beneficial.

To take advantage of this relative insensitivity, the optical inspection system can be designed so that a total optical path length traversed within the sample can equal, or can be relatively close to, an inverse of an expected scattering coefficient of the sample. For instance, the total optical path length traversed within the sample can be within 0.1%, within 1%, within 10%, or within 50% of an inverse of an expected scattering coefficient of the sample. Other suitable values can also be used. The expected scattering coefficient can represent a distribution of values of the scattering coefficient for a population of samples of the same type as the particular sample, such as human tissue.

The above analysis assumes a single scattering event within the sample. For geometries in which a detector element receives light that is largely due to a single high-angle scattering event, the above analysis also holds for multiple scattering events and finite positional and angular resolutions. The above analysis can also apply to confocal detection with a narrow collimated input and angularly-constrained output.

The above Detailed Description and Appendix are intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The invention claimed is:

1. An optical inspection system for optically characterizing a sample, comprising:
    an illuminator/collector assembly configured to deliver multiple incident light rays to the sample and collect multiple return light rays returning from the sample;
    a sensor that includes a plurality of zones, each zone measuring ray intensity as a function of ray position and ray angle for the respective collected return light rays;
    a ray selector configured to select a first subset of light rays from the collected multiple return light rays at the sensor that meet a first selection criterion, wherein the first selection criterion is associated with a single scattering event; and
    a computer including a characterizer configured to determine a physical property of the sample based on the ray intensities, ray positions, and ray angles for the first subset of light rays.

2. The optical inspection system of claim 1, wherein the first selection criterion comprises a first range of estimated path lengths traversed within the sample, a first range of path length distributions traversed within the sample, or a first range of estimated ray penetration depths traversed within the sample.

3. The optical inspection system of claim 1, wherein the ray selector is further configured to select a second subset of light rays from the collected return light rays that meet a second selection criterion; and
    wherein the characterizer is configured to determine the physical property based on the ray intensities, ray positions, and ray angles for the first subset of light rays and the second subset of light rays.

4. The optical inspection system of claim 3, wherein the first selection criterion comprises a first range of estimated path lengths or path length distributions, and the second selection criterion comprises a second range of estimated path lengths or path length distributions.

5. The optical inspection system of claim 3,
wherein the first selection criterion comprises traversing within the sample an estimated optical path length within a first range of optical path lengths,
wherein the second selection criterion comprises traversing within the sample an estimated optical path length within a second range of optical path lengths, and
wherein the second range of optical path lengths does not overlap the first range of optical path lengths.

6. The optical inspection system of claim 5,
wherein the ray intensities for the first subset of light rays are aggregated into a first binned signal,
wherein the ray intensities for the second subset of light rays are aggregated into a second binned signal, and
wherein the characterizer determines the physical property of the sample based on the first binned signal and second binned signal.

7. The optical inspection system of claim 6, wherein the ray selector includes first pixels of the sensor and second pixels of the sensor, the first pixels and the second pixels each having a shape and size configured for measuring the ray intensities for light rays within the first subset of light rays and the second subsets of light rays, respectively,
wherein the first pixels and the second pixels are configured to respectively output the first binned signal and the second binned signal.

8. The optical inspection system of claim 6, wherein the ray selector is further configured to:
receive signals from corresponding pixels of the sensor,
average a first subset of the signals to form the first binned signal, and
average a second subset of the signals to form the second binned signal.

9. The optical inspection system of claim 8, wherein the first and second subsets of the signals are averaged in hardware.

10. The optical inspection system of claim 8, wherein the first and second subsets of the signals are averaged in software.

11. The optical inspection system of claim 6, wherein the characterizer is further configured to:
fit the first and second binned signals to a Beer's Law calculation, and
determine an absorptivity of the sample based on the Beer's Law calculation.

12. The optical inspection system of claim 11, wherein the characterizer weights the first and second binned signals differently when determining the absorptivity of the sample.

13. The optical inspection system of claim 3, wherein the computer is configured to perform a first operation set using the first subset of light rays and perform a second operation set using the second subset of light rays in determining the physical property of the sample.

14. The optical inspection system of claim 1, wherein the sensor includes a plurality of microlenses and a detector positioned at a focal plane of the plurality of microlenses.

15. The optical inspection system of claim 14, further comprising a mask disposed between the plurality of microlenses and the detector, the mask including at least one blocking portion configured to block specified light rays in the collected return light rays.

16. The optical inspection system of claim 1, wherein the computer is configured to:
aggregate the ray intensities into binned signals, each binned signal corresponding to light rays in the collected return light rays that traverse within the sample an estimated optical path length within a respective range of optical path lengths,
wherein the characterizer is further configured to determine the physical property of the sample based on the binned signals.

17. The optical inspection system of claim 16, wherein the computer is further configured to:
fit the binned signals to a Beer's Law calculation; and
determine an absorptivity of the sample based on the Beer's Law calculation.

18. A method for optically characterizing a sample, comprising:
illuminating the sample with incident light using an illuminator;
collecting multiple return light rays returning from the sample;
measuring ray intensities as a function of ray position and ray angle for the respective collected return light rays using a sensor;
aggregating at least some of the ray intensities into a plurality of binned signals; and
determining a physical property of the sample based on the plurality of binned signals.

19. The method of claim 18, wherein each binned signal corresponds to the collected return light rays that traverse within the sample an estimated optical path length within a respective range of optical path lengths.

20. The method of claim 18, further comprising:
fitting the plurality of binned signals to a Beer's Law calculation; and
determining an absorptivity of the sample based on the Beer's Law calculation.

* * * * *